United States Patent [19]

Hedin et al.

[11] Patent Number: 5,042,480

[45] Date of Patent: Aug. 27, 1991

[54] METHOD AND IMPLANTABLE MEDICAL DEVICE FOR STIMULATING TISSUE CONTRACTIONS

[75] Inventors: Asa Hedin, Stockholm; Lennart Moberg, Spanga; Jan Ljungstroem, Solna, all of Sweden

[73] Assignee: Siemens Aktiengesellschaft, Munich, Fed. Rep. of Germany

[21] Appl. No.: 595,277

[22] Filed: Oct. 10, 1990

[30] Foreign Application Priority Data

Oct. 11, 1989 [EP] European Pat. Off. ............ 89118911

[51] Int. Cl.⁵ ............................................ A61N 1/365
[52] U.S. Cl. ............................................ 128/419 PG
[58] Field of Search ................................ 128/419 PG

[56] References Cited

U.S. PATENT DOCUMENTS

| | | | |
|---|---|---|---|
| 3,759,266 | 9/1973 | Lee et al. | 128/419 PG |
| 3,857,399 | 12/1974 | Zacouto | 128/419 PG |
| 3,881,493 | 5/1975 | Cannon et al. | 128/419 PG |
| 3,942,534 | 5/1976 | Allen et al. | 128/419 PG |
| 4,023,121 | 5/1977 | Alley, III | 128/419 PG |
| 4,052,991 | 10/1977 | Zacouto | 128/419 PG |
| 4,140,132 | 2/1979 | Dahl | 128/419 PG |
| 4,163,451 | 8/1979 | Lesnick et al. | 128/419 PG |
| 4,173,230 | 11/1979 | Digby | 128/419 PG |
| 4,428,378 | 1/1984 | Anderson et al. | 128/419 PG |
| 4,543,954 | 10/1985 | Cook et al. | 128/419 PG |
| 4,750,495 | 6/1988 | Moore et al. | 128/419 PG |

FOREIGN PATENT DOCUMENTS 0080348 6/1983 European Pat. Off. .
0313881 5/1989 European Pat. Off. .
0326629 8/1989 European Pat. Off. .

OTHER PUBLICATIONS

Physician's Manual for DIALOG 728 Pulse Generator Manufactured by Siemens-Elema AB, Feb., 1986.
Physician's Manual for Pulse Generator 704 Manufactured by Siemens-Elema AB, Mar. 1985.

*Primary Examiner*—William E. Kamm
*Attorney, Agent, or Firm*—Hill, Van Santen, Steadman & Simpson

[57] ABSTRACT

A medical device implantable into the body of a patient with which spontaneous tissue contractions can be detected and tissue contractions can be stimulated, generates a stimulation after the expiration of an adjustable first time interval, started by the respective detection or the stimulation of a tissue contraction, if a spontaneous tissue contraction is not detected before the expiration of the first time interval and if a shorter, second time interval, started by the detection or stimulation of a tissue contraction, has not yet expired. Detection of a spontaneous tissue contraction during the second time interval starts a new second time interval. The duration of the second time interval is automatically set such that it is always shorter by a defined amount than the duration of the first time interval.

19 Claims, 3 Drawing Sheets

METHOD AND IMPLANTABLE MEDICAL DEVICE FOR STIMULATING TISSUE CONTRACTIONS

BACKGROUND OF THE INVENTION

1. Field of the Invention

The present invention is directed to a medical device, and a method for operating the device, implantable in the body of a patient for stimulating tissue contractions, such as a cardiac pacemaker.

2. Description of the Prior Art

A pacemaker is known, and is described in the publication "DIALOG-Schrittmacher 728-Gebrauchsanweisung," October, 1986, Siemens-Elema AB, Solna, Sweden, which includes means for detecting spontaneous tissue contractions, means for stimulating tissue contractions and control means. The control means control the generation of stimulation pulses by the means for stimulating tissue contractions so that after the expiration of a first time interval, having an adjustable duration initiated by the detection or the stimulation of a tissue contraction, the means for stimulating is activated as long as a spontaneous tissue contraction, which initiates a new first time interval, has not been detected before the expiration of the first time interval. The detection of a spontaneous tissue contraction is prevented from starting a new first time interval during a second time interval which is initiated by the detection or stimulation of a tissue contraction, and which has a duration shorter than the duration of the first time interval. A new second time interval is initated upon the detection of a spontaneous tissue contraction during the second time interval.

In this known device, the duration of the first time interval, referred to as the base interval, corresponds to that stimulation frequency with which the device stimulates the heart in the absence of spontaneous heartbeats. In this known heart pacemaker, the duration of the first time interval as well as that of the second time interval are adjustable by a programming event independently of one another. The second time interval, referred to as the refractory time, is composed of two time segments. During the first segment of the second time interval, referred to as the absolute refractory time and whose duration is likewise adjustable on the basis of a programming event, the means for detecting are completely insensitive to any and all cardiac signals. This prevents tissue depolarizations occurring after the heart is charged with a stimulation pulse from causing mis-detections, i.e. from being incorrectly detected as a spontaneous heartbeat by the means for detecting. In the second, following segment of the second interval, referred to as the relative refractory time, spontaneous heartbeats that occur are in fact detected but a new base interval does not begin to run. Instead, the refractory time is again started over its full length. When, thus, the heart spontaneously beats so fast that the spontaneous heartbeats respectively appear within the relative refractory time, i.e., during the second segment of the second time interval, the known heart pacemaker switches from the VVI mode in which it normally operates into the VOO mode that corresponds to the asynchronous operating mode. The known heart pacemaker then stimulates the heart independently of the spontaneously occurring heartbeats with a stimulation frequency that corresponds to the duration of the base interval. This is advantageous since certain reentry tachycardia can thereby terminated. Mis-detections occurring during the relative refractory time as occur, for example, given a sensitivity of the means for detection that is set too high, moreover, can not start a new base interval. The appearance of misdetections can thus not prevent a stimulation of the heart that is required.

Based on the above, it is preferable to set a comparatively long refractory time in this known heart pacemaker. This has the consequence in practice, however, that the spontaneous heartbeat rate can rise to such an extent under a physical stress that the known heart pacemaker switches into its asynchronous operating mode, i.e. into the VOO mode, without a physiological reason for this switch being present. The heart of the patient is thus stimulated without this being actually required. This can lead to disturbances in heart rhythm. At any rate, the patient in whom the heart pacemaker is implanted is physically uncomfortable. Only an extremely experienced physician is in the position-taking the individual requirements and peculiarities of the respective patient into consideration-of programming the duration of the refractory time for a defined base interval such that, first, injurious consequences of mis-detections and external disturbances are avoided and, second, a physiologically unfounded transition of the heart pacemaker into its asynchronous operating mode is impossible. The above considerations also analogously apply to heart pacemakers working the SSI or DDD mode, whereby the risk of the physiologically unfounded transition respectively into the SOO or AOO mode is present.

SUMMARY OF THE INVENTION

An object of the invention is to a device and a method of the type described above wherein provide it is assured that the duration of the second time interval is long enough to avoid injurious consequences of mis-detections and is short enough to avoid basically unnecessary stimulations of tissue contractions, particularly given high physical activity of the patient.

In a first embodiment of the invention, the above object is achieved in a device and method wherein the duration of the second time interval is set dependent on the set duration of the first time interval, such that the duration of the second time interval is shorter by a defined amount than the set duration of the first time interval. By contrast to the prior art wherein the duration of the first as well as the duration of the second time interval must be defined and set by the physician, it is adequate in the invention for the physician to set the duration of just the first time interval. The duration of the second time interval is then automatically set by the control means dependent on the set duration of the first time interval such that the duration of the second time interval is shorter by a defined amount than that of the first time interval. Given a suitable selection of the defined amount, it is thus assured that the second time interval is long enough to prevent, for example, mis-detections from starting a new first time interval. It is also practically impossible, given a suitable selection of the defined amount, that the device will switch into its asynchronous operating mode given high physical activity of the patient without there being any physiological reason for doing so. It is also assured that, given a reprogramming of the duration of the first time interval after the implantation of the device, the required correction of the duration of the second interval always ensues without action on the part of the attending physician being required for this purpose.

In a further modification of the method and device, a contraction frequency matched to the respective physical activity of the patient is calculated, and the control means set the duration of the second time interval such that first, its chronological curve at least essentially following the chronological curve of the period duration corresponding to the calculated, matched contraction frequency but is shorter than this period duration, and second, it is always shorter than the set duration of the first time interval. By contrast to the prior art wherein the duration of the second time interval is in fact normally programmable but has a fixed value during the normal operation of the device, the duration of the time interval in the invention varies dependent on the calculated contraction frequency matched to the physical activity of the patient, such that its chronological curve follows the period duration that corresponds to the respectively calculated, matched contraction frequency and is shorter than it. This assures that the second time interval is long enough to prevent misdetections from starting a new first time interval. Because the duration of the second time interval is oriented on the contraction frequency respectively matched to the physical activity of the patient, it is impossible for the device to switch into its asynchronous operating mode given high physical activity of the patient without a physiological reason to do so. This risk is further reduced because the duration of the second time interval is shorter than the period duration that corresponds to the calculated, matched contraction frequency.

A preferred modification of the invention provides that the means for calculating the matched contraction frequency comprise a sensor means for forming a signal corresponding to the physical activity and that the control means calculate the matched contraction frequency with reference to the signal of the sensor means. A temperature sensor and method for calculating a contraction frequency matched to the physical activity of the patient are disclosed in U.S. Pat. No. 4,543,954, and it is well known to alter the pacing rate using a piezoelectric sensor as disclosed in U.S. Pat. Nos. 4,140,132 and 4,428,378.

In a preferred embodiment of the invention the means for calculating the matched contraction frequency comprise means for calculating the repetition rate of immediately successive, spontaneous tissue contractions and the control means use the calculated repetition rate as the calculated, matched contraction frequency. This embodiment is particularly suited for therapy cases wherein physiological correct, spontaneous tissue contractions of the patient occur during longer periods, these representing a direct measure for the contraction frequency matched to the respective physical activity.

In a further modification of the invention the control means set the duration of the second time interval such that it is shorter by a defined amount than the period duration that corresponds to the calculated, matched contraction frequency. A further modification of the invention provides that the defined amount is variable. The attending physician is thus in the position to set the defined amount in accord with the requirements of the individual patient and the treatment case. This can be accomplished by non-invasive programming in a known way such that the physician can also vary the defined amount after the implantation of the device.

The aforementioned "defined amount" may correspond to a defined percentage, for example 20% of the duration of the first time interval, of the period duration that corresponds to the calculated, matched contraction frequency. The defined amount may alternatively correspond to a defined amount of the frequency by which the frequency corresponding to the duration of the second time interval is higher than the frequency corresponding to the duration of the first time interval, than the calculated, matched contraction frequency. A duration of the second time interval is thus always set that corresponds to a frequency that, for example, is 10 Hz higher than the calculated, matched contraction frequency, or than the frequency corresponding to the duration of the first time interval. This has the advantage that the size of the defined amount is especially easily surveyable by the attending physician. In order to guarantee an even more enhanced surveyability, it is preferable to fashion the control means such that the defined amount of the frequency can be recited in units which are standard in the medical field, which may be other than Hertz. In the case of cardiology, for example, the unit of heartbeats per minute (bpm) should be selected.

In a further embodiment of the invention the control means set the duration of the first time interval such that it corresponds to the period duration that corresponds to the calculated, matched contraction frequency. Since the contraction frequency matched to the physical activity of the patient is already calculated within the framework of the invention, it is thus possible with minimum outlay to set the duration of the first time interval to assure that the stimulation of tissue contractions as needed ensues with a stimulation frequency adapted to the physical activity of the patient. The inventive concepts disclsoed herein may be used in a heart pacemaker, wherein the means for detecting detect spontaneous heart muscle contractions, the means for stimulating stimulate heart muscle contractions, and the means for calculating a contraction frequency matched to the physical activity of the patient calculate the heartbeat rate or the spontaneous heartbeat rate of the patient matched to the respective physical activity of the patient.

DESCRIPTION OF THE PREFERRED EMBODIMENTS

Figure 1:
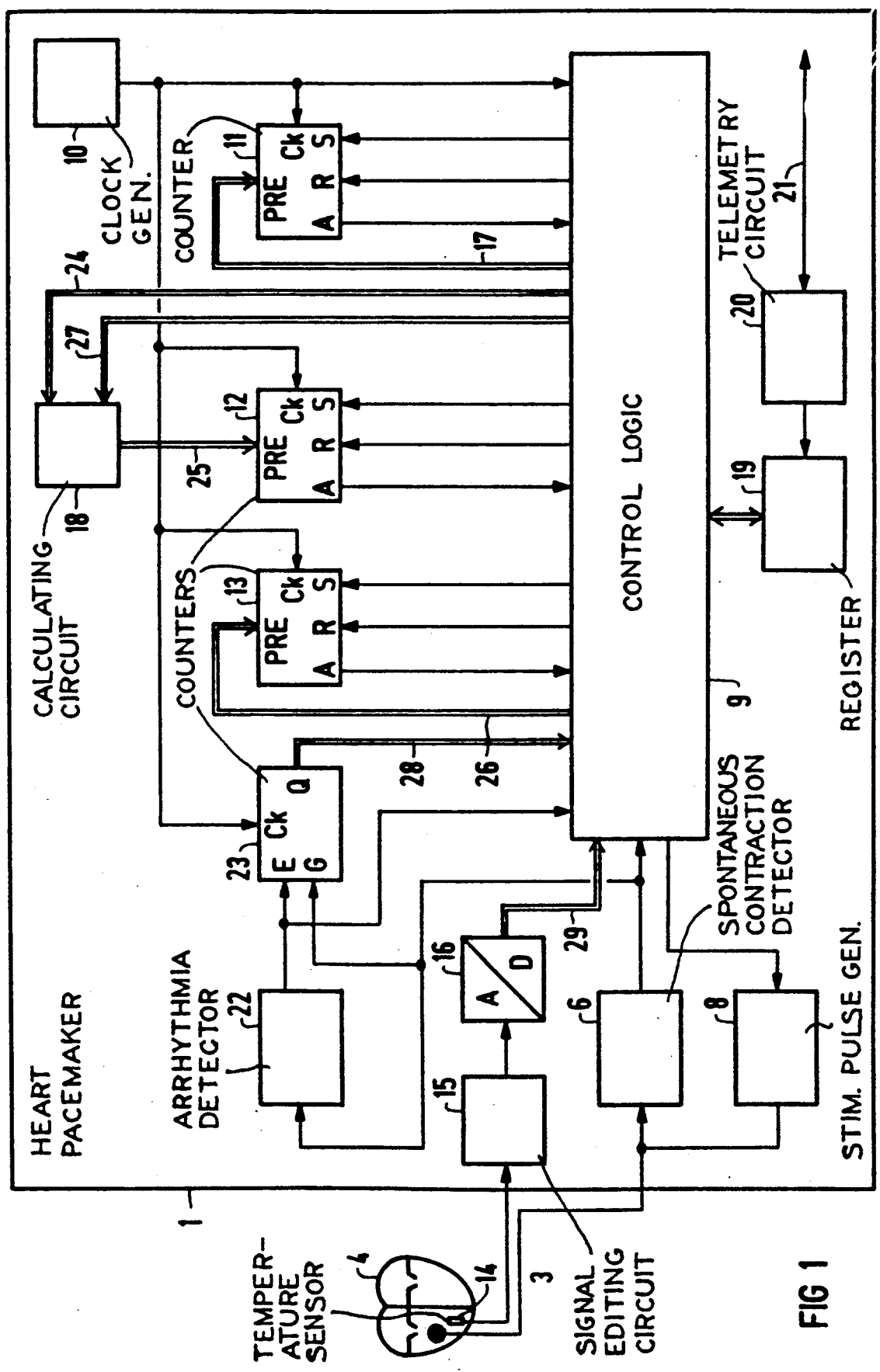
FIG. 1 a block circuit diagram of a heart pacemaker constructed in accordance with the principles of the invention.

FIG. 1 shows a heart pacemaker in accordance with the principles of the invention operable in the VVI mode: The heart pacemaker has electronics arranged in a hermetically tight, implantable housing 1 and is in electrical contact via an endocardial electrode 3 with the schematically indicated heart 4 of the patient in whom the heart pacemaker is implanted. The electrode 3 is guided through the vein system to the heart 4 of the patient and is anchored in the right ventricle of the heart 4.

The electrode 3 is in communication with a detector 6 which detects spontaneous heart muscle contractions in the region of the ventricle. The electrode 3 is also connected to a stimulation pulse generator 8 for stimulating heart muscle contractions in the region of the ventricle.

The interaction of the detector 6 and the stimulation pulse generator 8 with the heart 4 is controlled by control logic 9 to which a clock generator 10, a PP counter 11, an R counter 12 and an RA counter 13 are connected. The counters 11, 12, 13 are of the type known as preset counters. Such a counter to which the clock pulses are supplied via a corresponding input Ck, counts a plurality of clock pulses during a counting event, this plurality being defined by data supplied to an input of the counter referenced PRE. When the defined number of clock pulses is reached, the counter generates an appropriate signal at its output A. Such a counter begins a counting event when a start pulse is supplied to an input referenced S. The counting event is aborted and/or the counter is reset when a reset pulse is supplied to an input R. In the case of the described heart pacemaker, the counters 11, 12, 13 receive receive start and reset pulses from the control logic 9. The counters 11, 12, 13 receive their clock pulses from the clock generator 10.

The operation of the heart pacemaker shall be set forth below only to an extent as required in conjunction with the present invention. The publications "Pulse Generator 704-Physicians Manual", Siemens-Elema AB, Solna, Sweden, March 1985 and "DIALOG Schrittmacher 728-Gebrauchsanweisung", Siemens-Elema AB, Solna Sweden, October 1986, may be consulted for further information.

When a spontaneous heart muscle contraction in the region of the ventricle is detected by the detector 6, a corresponding signal proceeds from the detector 6 to the control logic 9. In response thereto, the latter starts the PP counter 11 which, as mentioned, receives its clock pulses from the clock generator 10. The clock generator 10 is an oscillator, for example a crystal oscillator, which generates clock pulses at a defined clock frequency. These clock pulses are also supplied to the control logic 9. When the PP counter 11 has counted a plurality of clock pulses corresponding to the duration of a first time interval, referred to as the base or PP interval, a corresponding signal proceeds from its output to the control logic 9. This first time interval can be programmed by data supplied to the PRE input of the PP counter II on line 17 from the control logic 9 in a manner described below. In response to the signal from the PP counter II, the control logic 9 activates the stimulation pulse generator 8 to cause the generation of a stimulation pulse that effects the stimulation of a heart muscle contraction in the region of the ventricle. Simultaneously, the control logic 9 resets the PP counter 11 and restarts it. The output of a stimulation pulse by the stimulation pulse generator 8 is suppressed, however, if the detector 6 has detected a spontaneous heart muscle contraction in the region of the ventricle during the base interval. If the control logic 9 receives a signal from the detector 6 during the base interval, it resets the PP counter 11 and restarts it.

As soon as the repetition rate of the spontaneous heartbeats drops below a repetition rate that corresponds to the duration of the base interval, the heart is thus stimulated such that a heartbeat rate corresponding at least to the duration of the base interval is present.

The PP counter 11 is not reset and restarted, however, in the described way by every detection during the base interval. For this to occur, a second time interval, referred to as the refractory time, must have expired. The refractory time is calculated with the R counter 12. When the detector 6 detects a spontaneous heart muscle contraction in the region of the ventricle and when a corresponding signal proceeds from the detector 6 to the control logic 9, or when the control logic 9 activates the stimulation pulse generator 8 to generate a stimulation pulse, the control logic 9 starts the R counter 12. The R counter 12 receives its clock pulses from the clock generator 10. When the R counter 12 has counted a plurality of clock pulses corresponding to the duration of the refractory time, which is adjustable as described below by data supplied to its input PRE, a corresponding signal proceeds from its output to the control logic 9. Only after the arrival of this signal does a spontaneous heart muscle contraction detected with the detector 6 during the running base interval cause the control logic 9 to reset and restart the PP counter 11. If, by contrast, the detector 6 detects a spontaneous heart muscle contraction before the signal indicating the end of the refractory time proceeds from the R counter 12 to the control logic 9, the control logic 9 resets the R counter 12 and restarts it, so that the refractory time begins to run anew. Since a resetting and renewed starting of the PP counter 11 by the control logic 9 is suppressed in this case, the control logic 9 activates the stimulation pulse generator 8 after the expiration of the base interval to generate a stimulation pulse unless a spontaneous heart muscle contraction has again been detected by the detector 6 after the expiration of the restarted refractory time and before the expiration of the running base interval.

The resetting and restarting of the R counter 12, moreover, only ensues during a second segment of the refractory time, referred to as the relative refractory time. The first segment of the refractory time that precedes the relative refractory time is referred to as the absolute refractory time.

No detections whatsoever are possible during the absolute refractory time. This is achieved in the described exemplary embodiment in that the control logic 9 ignores signals from the detector 6 and indicating a detection during the absolute refractory time. The absolute refractory time is calculated with the RA counter 13. When the detector 6 detects a spontaneous heart muscle contraction in the region of the ventricle and when a corresponding signal proceeds from the detector 6 to the control logic 9, or when the control logic 9 activates the stimulation pulse generator 8 to generate a stimulation pulse, the control logic 9 starts the RA counter 13. The RA counter 13, as the PP counter 11 and the R counter 12, receives its clock pulses from the clock generator 10. When the RA counter 13 has counted a plurality of clock pulses corresponding to the duration of the absolute refractory time, which is programmable as described below by data supplied to its input PRE via the data line 26 by the control logic 9, a corresponding signal proceeds from the output of the RA counter 13 to the control logic 9. This means that the absolute refractory time has expired and the relative refractory time is running, which means that the control logic 9 is enabled to accept signals from the detector 6. Signals proceeding from the detector 6 to the control logic 9 during the absolute refractory time thus do not lead to a resetting and restarting of the PP counter 11 or of the R counter 12.

The heart pacemaker thus switches into the asynchronous mode (VOO mode) wherein it stimulates the heart with a stimulation frequency corresponding to the set or programmed duration of the base interval independently of possible detections of spontaneous heartbeats, when the detection of successive, spontaneous heartbeats ensues during the relative refractory time.

By contrast to heart pacemakers of the prior art wherein the duration of the base interval and the duration of the refractory time must be separately set by the attending physician during the course of the programming, it is provided in a first operating mode of the heart pacemaker of the invention that the duration of the refractory time is set dependent on the programmed duration of the base interval such that the duration of the refractory time is shorter by a defined amount than that of the base interval. It is thereby provided that the duration of the absolute refractory time is in fact programmable but retains a fixed value. For example, if the duration of the refractory time is shorter than the duration of the programmed base interval by a defined amount of 100 ms and if a duration of 125 ms is set for the absolute refractory time, a duration of 900 ms is set for the refractory time given a duration of the base interval of 1000 ms. The duration of the refractory time then amounts to 900 ms, the duration of the relative refractory time amounts to 775 ms and the duration of the absolute refractory time amounts to 125 ms, as programmed.

For a programmed duration of the base interval of 900 ms, a duration of 800 ms for the refractory time, a duration of 675 ms for the relative refractory time and the programmed value of 125 ms for the duration of the absolute refractory time correspondingly derive. Given a suitable selection of the defined amount adapted to the respective treatment case it is thus assured that, first, the refractory time is long enough to prevent mis-detections or external disturbances from starting a new base interval without a spontaneous heartbeat having in fact occurred and, second, the refractory time does not last so long that the device switches into the asynchronous operating mode given high physical activity of the patient without such a switch being physiologically required.

Figure 2:
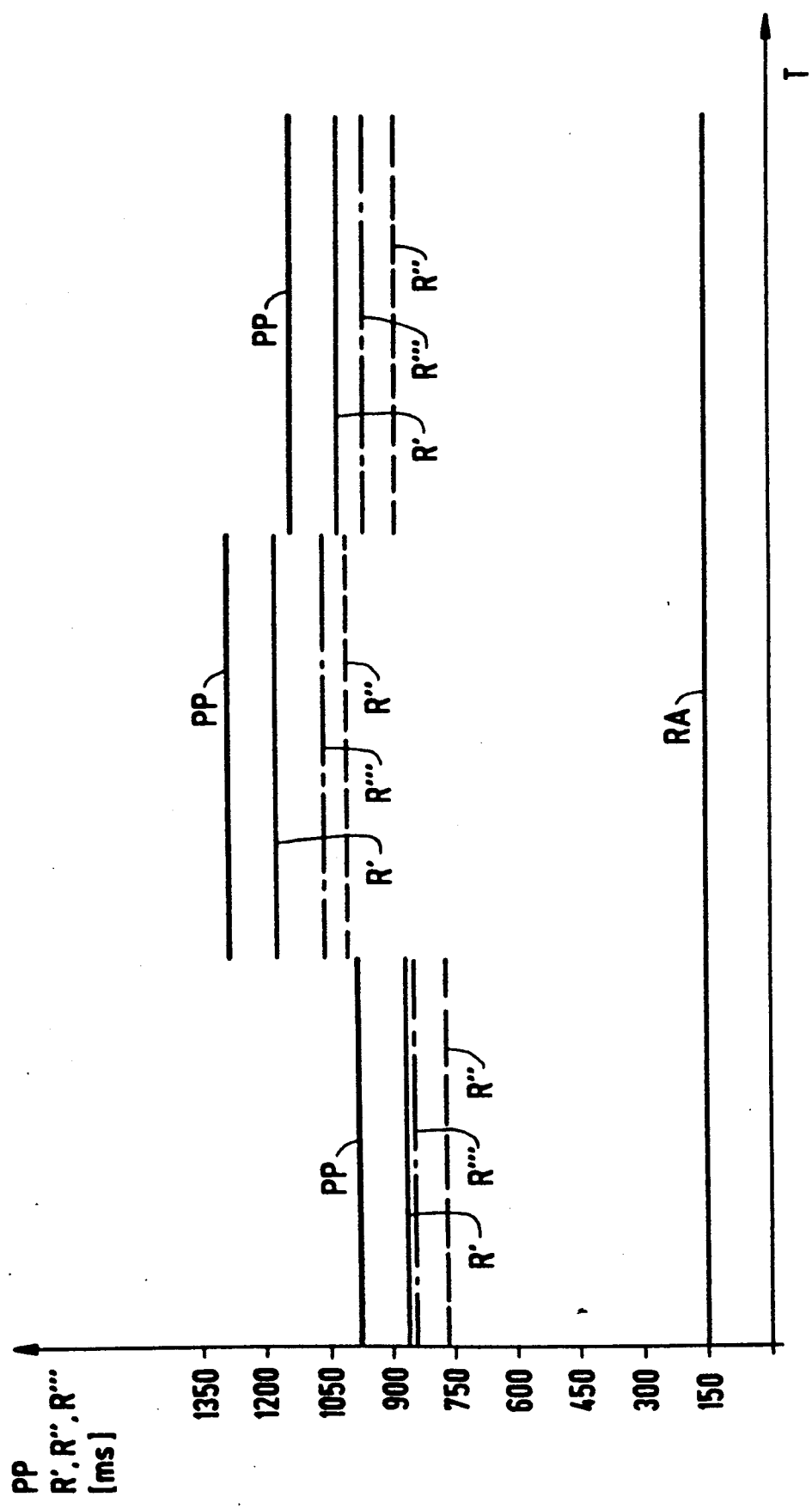
FIG. 2 and 3 two diagrams illustrating different operating modes of the heart pacemaker of FIG. 1.

The conditions corresponding to the first operating mode are qualitatively shown in FIG. 2 over the time T for three different programmings of the heart pacemaker. A duration of 975 ms of the base interval PP is thereby initially programmed, this being lengthened to 1275 ms in the course of a reprogramming and being shortened to 1175 ms in the course of a further reprogramming. The duration of the absolute refractory time RA amounts to 150 ms in all cases. The refractory times R′, R″ and R‴ are also entered in FIG. 2 respectively for three different values of the defined amount by which the refractory time is shorter than the set duration of the base interval PP. The refractory times R′ derive when the set refractory time is shorter by a defined amount of the time than the set duration of the base interval PP, 120 ms in the case of the example shown in FIG. 2. The refractory times R″ derive when the duration of the refractory time is shorter by a defined percentage than the programmed duration of the base interval PP, 25% in the case of the examples shown in FIG. 2. The refractory times R‴ derive in that the heartbeat rate corresponding to the programmed duration of the base interval PP increases by a defined amount of the frequency, 15 bpm (beats per minute) in the case of the examples shown in FIG. 2, and the corresponding period duration which then corresponds to the respective refractory R‴ is calculated.

As may be seen from FIG. 1, the heart pacemaker of the invention has a telemetry register 19 connected to the control logic 9 and a telemetry circuit 20 connected to this telemetry register 19. As a result the heart pacemaker can exchange data bidirectionally with an external device (not shown), referred to as a programmer, as indicated by the double arrow 21. There is thus also the possibility of programming the heart pacemaker after implantation. Among other things, the duration of the base interval and the duration of the absolute refractory time can be set with the programmer via the telemetry circuit 20 and the telemetry register 19, whereby the corresponding data are supplied from the control logic 9 in the described way to the input PRE of the PP counter 11 via the data line 17 and to the input PRE of the RA counter 13 via the data line 26. There is also the possibility of programming the defined amount by which the duration of the refractory time is shorter than the programmed duration of the base interval, such that the defined amount corresponds either to a defined time amount, to a defined percentage or to a defined amount of the rate, as was set forth in conjunction with FIG. 2. There is also the possibility of programming the defined amount simply as a selected amount, without reference to another parameter.

The control logic 9 then calculates the plurality of clock pulses of the clock generator 10 which corresponds to the programmed, defined amount in terms of type and amount and conducts the corresponding data via a data line 24 to a digital calculating circuit 18. The latter subtracts the plurality of clock pulses corresponding to the programmed, defined amount from the plurality of clock pulses of the clock generator 10 corresponding to the programmed duration of the base interval. As output data, the calculating circuit 18 thus supplies data defining the plurality of clock pulses that corresponds to the refractory time to be set. Accordingly, a first input of the calculating circuit 18 is supplied with those data that correspond to the duration of the base interval, by the control logic 9 via a data line 27. In the first operating mode this is the same data supplied to the input PRE of the PP counter 11 via the data line 17. The data line 24 is connected to a second input of the calculating circuit 18. The output of the calculating circuit 18 is connected via a data line 25 to the input PRE of the R counter 12. The duration of the refractory time is thus set dependent on the programming of the heart pacemaker in one of the ways set forth in conjunction with FIG. 2.

By contrast to the above-described operating mode of the heart pacemaker wherein the duration of the refractory time has a fixed value for a defined programming of the heart pacemaker, it is provided in the case of a second operating mode of the heart pacemaker of the invention, to which the heart pacemaker can be switched with the programmer, that the duration of the refractory time has its chronological curve at least essentially following the period duration of a heartbeat rate (whose calculation is set forth below) matched to the physical activity of the patient wearing the heart pacemaker, and is shorter than this period duration by a defined amount. Given a suitable selection of the defined amount adapted to the treatment case, this measure insures that, taking the momentarily existing physical activity of the patient into consideration, the refractory time, first, is adequately long enough to prevent mis-detections or disturbances from starting a new base interval without a spontaneous heartbeat having in fact occurred and, second, the refractory time does not last so long that the device switches into the asynchronous operating mode given high physical activity of the patient without such a switch being physiologically required.

Figure 3:
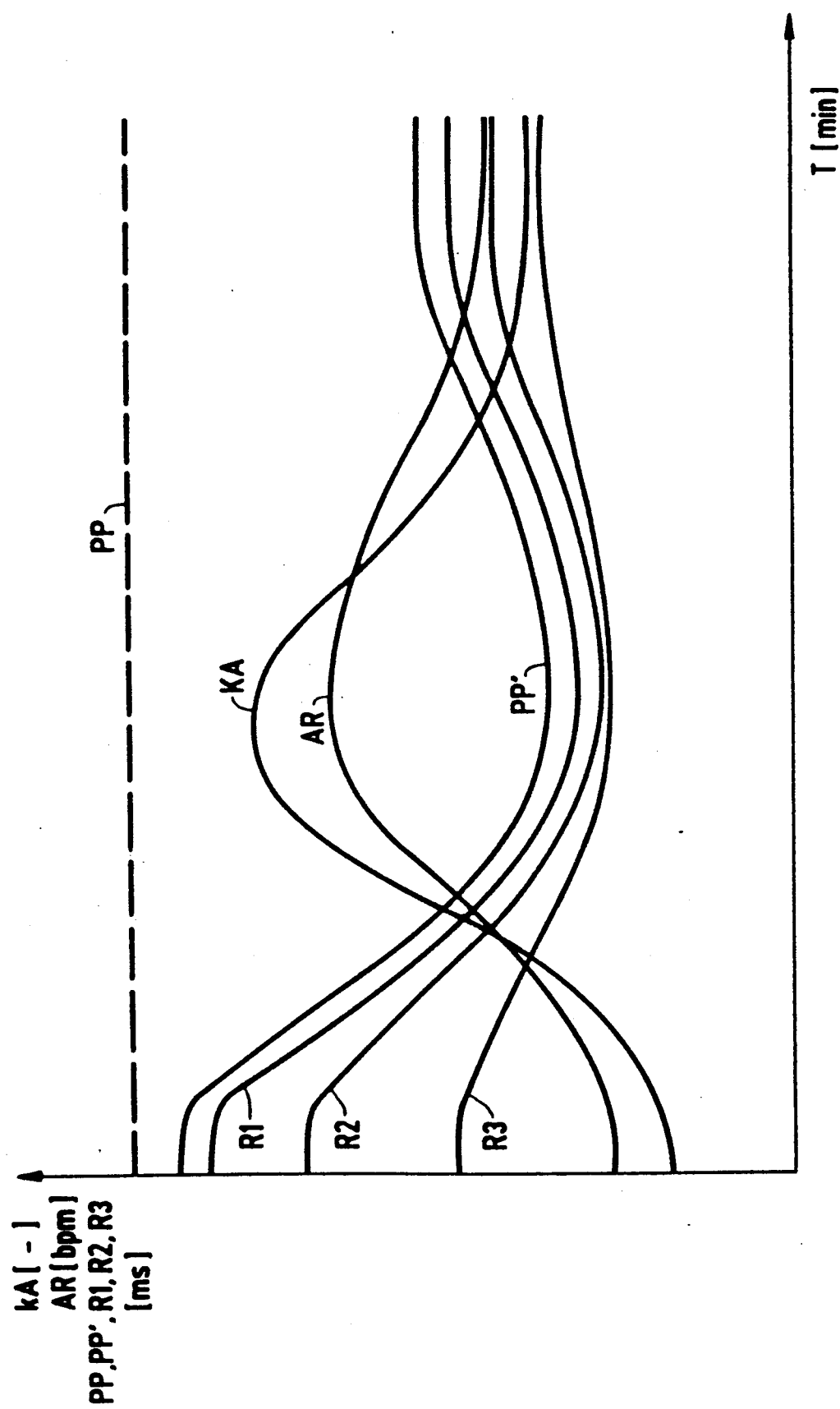

The conditions corresponding to the second operating mode are qualitatively shown in FIG. 3. FIG. 3 shows the curves of the physical activity KA of a patient without specification of a unit of measurement, of the heartbeat rate AR in bpm adapted to this physical activity, the curve of the adapted heartbeat rate AR corresponding to the period duration PP' in ms and three different curves R1, R2 and R3 of the refractory time in ms over the time T in minutes. The programmed duration of the base interval PP in ms, which is constant over the time T, is also entered with broken lines in FIG. 3. In the case of FIG. 3, the physical activity KA of the patient initially increases from a relatively low level and then drops and stabilizes at a somewhat higher level. This course of the physical activity KA is reflected in the corresponding curves of the matched heartbeat rate AR and of the period duration PP' corresponding thereto. This also applies to the curves of the refractory time R1, R2 and R3. The curve R1 of the refractory time derives when the set refractory time is shorter by a defined amount, 50 ms in the example, than the period duration PP' that corresponds to the matched heartbeat rate AR. The curve R2 of the refractory time derives when the duration of the refractory time is shorter by a defined percentage, 20% in the illustrated example, than the period duration PP' that corresponds to the matched heartbeat rate AR. The curve R3 of the refractory time derives in that the matched heartbeat rate AR is increased by a defined amount of the frequency, 50 bpm in the example, and the corresponding period duration that corresponds to the refractory time R3 is calculated. The refractory times R1, R2, R3 are in all three instances always shorter than the programmed duration of the base interval PP and shorter than the period duration PP' corresponding to the matched heartbeat rate AR.

In order to be able to calculate the heartbeat rate matched to the physical activity of the patient, which is a prerequisite for the control of the refractory time set forth in conjunction with FIG. 3, a schematically indicated temperature sensor 14 is attached to the electrode 3 leading into the right ventricle of the heart in the heart pacemaker of the invention. The temperature sensor 14 measures the temperature of the venous blood situated in the right ventricle, which, as is known, represents a measure of the physical activity of the patient. Via a line proceeding parallel to the electrode 3, the temperature sensor 14 is in communication with a signal editing circuit 15 from which the signal acquired with the temperature 14 and corresponding to the physical activity of the patient proceeds to an analog-to-digital converter 16. When the heart pacemaker is programmed to the operating mode of FIG. 3, the control logic 9 uses the output data of the analog-to-digital converter 16 supplied to it via the data line 29 to calculate the heartbeat rate matched to the respective physical activity of the patient, according to an algorithm as disclosed, for example, by U.S. Pat. No. 4,543,954. The control logic 9 also calculates that plurality of clock pulses of the clock generator 10 which occurs between two successive heartbeats given the matched heartbeat rate. Instead of the data corresponding to the duration of the base interval in the case of the operating mode of FIG. 2, the control logic 9 in the operating mode of FIG. 3 conducts data regarding this plurality of clock pulses via the data line 27 to the first input of the calculating circuit 18. In the operating mode of FIG. 3, the calculating circuit 18 subtracts the plurality of clock pulses corresponding to the selected, defined amount by which the duration of the refractory time should be shorter than the period duration corresponding to the calculated, matched heartbeat rate from the plurality of clock pulses. The control logic 9 again supplies the data regarding that plurality of clock pulses corresponding to the defined amount in terms of nature and amount to the second input of the calculating circuit 18 via the data line 24. As already mentioned, the output data of the electronic calculating circuit 18 that correspond to the difference between the two pluralities of clock pulses are supplied to the input PRE of the R counter 12 via the data line 25. A control of the duration of the refractory time dependent on the physical activity of the patient in the way set forth in conjunction with FIG. 3 thus ensues, whereby the absolute refractory time (not entered in FIG. 3), as the base interval PP, has a constant duration after the programming of the device has been carried out.

In a third operating mode of the heart pacemaker, to which it can be switched with the programmer and that otherwise corresponds to the second operating mode, the control logic 9, instead of supplying the input PRE of the PP counter 11 with data corresponding to a permanently programmed duration of the base interval PP, supplies the input PRE of the PP counter 11 via the data line 17 with data indicating the plurality of clock pulses corresponding to the period duration PP' of the calculated, matched heartbeat rate AR. This causes the stimulation pulse generator 8 to stimulate heart muscle contractions in the region of the ventricle with a repetition rate that corresponds to the calculated, matched heartbeat rate AR in case the repetition rate of the detected, spontaneous heart muscle contractions in the region of the ventricle falls below the heartbeat rate AR adapted to the physical activity KA of the patient. This is because the duration of the first time interval, i.e. of the base interval, in the third operating mode is identical to the period duration PP' of the calculated, matched heartbeat rate AR. It is thus additionally insured that the heartbeat rate of the patient can not drop below the heartbeat rate AR matched to the physical activity KA of the patient. The matched heartbeat rate AR is downwardly limited by a lower limit value, for example 60 bpm, and is upwardly limited by an upper limit value, for example 140 bpm, which define a physiologically meaningful range. The limit values can be programmed in accord with the individual requirements of every patient.

The heart pacemaker of the invention also includes an arrhythmia detector 22 to which the output signal of the detector 6 is supplied. The arrhythmia detector 22 (a suitable detector is disclosed by U.S. Pat. No. 3,861,387) delivers an output signal when a cardiac arrhythmia is present, i.e. when the heart 4 does not beat following the sinus rhythm. The output signal of the arrhythmia detector 22 is also supplied to the enable input E of a counter 23 and disenables the counter 23 as long as a cardiac arrhythmia is present. The gate input G of the counter 23 is supplied with the output signal of the detector 6. The clock input Ck of the counter 23 is connected to the clock generator 10. When the heart 4 beats following the sinus rhythm, the counter 23 thus counts that plurality of clock pulses that occurs between two successive, spontaneous heartbeats. The data available at the output Q of the counter 23 thus correspond to the chronological duration between two successive, spontaneous heartbeats and thus represent a measure for the spontaneous heartbeat rate. As long as the heart 4 beats following the sinus rhythm, the output data of the counter 23 directly represent a measure for the heartbeat rate adapted to the physical activity of the patient. These data are supplied via a data line 29 to the control logic 9 which, in the second and third operating modes of the heart pacemaker and as long as the output signal of the arrhythmia detector 22 indicates that the heart 4 is beating following the sinus rhythm, uses the data as the heartbeat rate matched to the physical activity of the patient.

During periods wherein the heart 4 beats following the sinus rhythm, the output data of the analog-to-digital converter 16 are thus not used by the control logic 9 for calculating the heartbeat rate matched to the physical activity of the patient, neither for setting the duration of the base interval nor the duration of the refractory time. On the contrary, the control logic 9 supplies the output data of the counter 23, or data derived therefrom, for example a chronological average, to the input PRE of the PP counter 11 via the data line 17 and to the first input of the electronic calculating circuit 18 via the data line 27. As long as the heart 4 beats following the sinus rhythm, thus, the heartbeat rate matched to the physical activity of the patient is not calculated via an algorithm that would be necessarily affected by imprecisions but is instead calculated by direct measurement of the existing heartbeat rate. This is the most physiologically correct way. The heartbeat rate AR entered in FIG. 2 and matched to the physical activity can thus be based on both the heartbeat rate calculated according to an algorithm with reference to the output data of the analog-to-digital converter 16 and the measured, actual heartbeat rate, dependent upon whether a cardiac arrhythmia is present or the heart 4 beats following the sinus rhythm. When an arrhythmia arises, i.e. when the heart 4 needs stimulation, the durations of the base interval and of the refractory time most recently set on the basis of the actually existing heartbeat rate are retained for a defined plurality of successive stimulation pulses, for example 30 stimulation pulses. When a continuous plurality of stimulation pulses that exceeds the defined plurality is required, the control logic 9 utilizes the output data of the analog-to-digital converter 16 for calculating the duration of the base interval and of the refractory time.

When the heart pacemaker of the invention is implanted in a patient whose heartbeats following the sinus rhythm only during short periods or not at all, or when this is desired for some other reason, there is the possibility of programming the heart pacemaker so that the output data of the counter 23 remain fundamentally out of consideration.

It is also possible within the framework of the invention to entirely forego the arrhythmia detector 23 and the counter 24. There is also the possibility of also foregoing the temperature sensor 14, the signal editing circuit 15 and the analog-to-digital converter 16. The heart pacemaker then operates exclusively according to the first operating mode set forth with reference to FIG. 2.

Although the invention has been set forth with reference to a heart pacemaker operating in the VVI mode, it can also be analogously employed in other heart pacemakers. The invention is particularly advantageous in conjunction with heart pacemakers operating in the DDD mode since the risk is then present, that the heart pacemaker will switch into the AOO mode as a consequence of "far field R-oversensing" is effectively countered. "Far field R-oversensing" means that the QRS complex is acquired by the atrial electrode as a consequence of R-potential propagation emanating from the ventricle.

The described, specific structure of the heart pacemaker is to be understood only as an example. The functions important to the invention can also be realized given a different structure of the heart pacemaker.

The invention has been set forth above with reference to the example of a heart pacemaker. However, it can also be utilized in other tissue stimulators.

Although other modifications and changes may be suggested by those skilled in the art, it is the intention of the inventors to embody within the patent warranted hereon all changes and modifications as reasonably and properly come within the scope of their contribution to the art.

We claim as our invention:

1. A medical device adapted for implantation in the body of a patient, said device comprising:
    means for detecting spontaneous tissue contractions at a site in said patient;
    means for stimulating tissue contractions at said site;
    means for activating said means for stimulating at the end of a first time interval of selectable duration if a spontaneous contraction is not detected during said first time interval, each spontaneous or stimulated contraction starting a new first time interval;
    means for preventing a spontaneous contraction from starting a new first time interval if said spontaneous contraction occurs during a second time interval, said second time interval starting with the spontaneous or stimulated contraction which starts said first time interval and said means for preventing starting a new second time interval upon the detection of a spontaneous contraction during said second time interval, said second time interval having a duration shorter than the duration of said first time interval; and
    means, when the duration of said first time interval is selected, for automatically setting the duration of said second time interval dependent on the duration of said first time interval so that said second time interval is shorter than said first time interval by a defined amount.

2. A medical device as claimed in claim 1 further comprising means for adjusting said defined amount.

3. A device as claimed in claim 1 wherein said means for automatically setting the duration of said second time interval is a means for automatically setting the duration of said second time interval as a defined percentage of the duration of said first time interval.

4. A device as claimed in claim 1 wherein said first time interval has a period defining a frequency of said first time interval and wherein said second time interval has a period defining a frequency of said second time interval, and wherein said means for automatically setting the duration of said second time interval is a means for automatically setting the frequency of said second time interval so that said frequency of said second time interval is higher by said defined amount than said frequency of said first time interval.

5. A device as claimed in claim 1 wherein said means for preventing a spontaneous contraction includes means for dividing said second time interval into successive first and second sub-intervals, said first sub-interval having a fixed duration and said second sub-interval having a duration which is set dependent on the duration of said first time interval by said means for automatically setting the duration of said second time interval and wherein said means for preventing a spontaneous contraction from starting a new first time interval starts a new second time interval only if a spontaneous tissue contraction is detected during said second sub-interval.

6. A device as claimed in claim 1 wherein said device is a heart pacemaker, wherein said means for detecting spontaneous tissue contractions is a means for detecting spontaneous heart muscle contractions, and wherein said means for stimulating tissue contractions is a means for stimulating heart muscle contractions.

7. A medical device adapted for implantation in the body of a patient, said device comprising:
  means for detecting spontaneous tissue contractions at a site in said patient;
  means for stimulating tissue contractions at said site;
  means for activating said means for stimulating at the end of a first time interval of selectable duration if a spontaneous contraction is not detected during said first time interval, each spontaneous or stimulated contraction starting a new first time interval;
  means for preventing a spontaneous contraction from starting a new first time interval if said spontaneous contraction occurs during a second time interval, said second time interval starting with the spontaneous or stimulated contraction which starts said first time interval and said means for preventing starting a new second time interval upon the detection of a spontaneous contraction during said second time interval, said second time interval having a duration shorter than the duration of said first time interval;
  means for calculating a tissue contraction frequency matched to the physical activity of said patient, the matched contraction frequency having a chronological curve associated therewith; and
  means, when the duration of said first time interval is selected, for automatically setting the duration of said second time interval dependent on the duration of said first time interval so that said second time interval has a chronological curve substantially following said chronological curve of said matched contraction frequency and a duration which is always shorter than said first time interval.

8. A device as claimed in claim 7 wherein said means for calculating a tissue contraction frequency matched to the physical activity of said patient includes sensor means for obtaining an electrical signal corresponding to the physical activity of said patient, and wherin said means for calculating a tissue contraction frequency includes means for calculating said tissue contraction frequency based on said signal from said sensor means.

9. A device as claimed in claim 7 wherein said means for calculating a tissue contraction frequency matched to the physical activity of said patient includes means for identifying the repetition rate of immediately successive tissue contractions and wherein said means for calculating uses said repetition rate as said tissue contraction frequency.

10. A device as claimed in claim 7 wherein said means for automatically setting the duration of said second time interval is a means for setting the duration of said second time interval so that said second time interval is shorter by a defined amount than the period of said matched contraction frequency.

11. A medical device as claimed in claim 10 further comprising means for adjusting said defined amount.

12. A device as claimed in claim 10 wherein said means for setting the duration of the second time interval so that said second time interval is shorter by a defined amount than the period corresponding to the matched contraction frequency is a means for setting the duration of said second time interval as a defined percentage of the period corresponding to the matched contraction frequency.

13. A device as claimed in claim 10 wherein said second time interval has a period defining a second time interval frequency, and wherein said means for setting the duration of said second time interval is a means for setting the duration of the second time interval so that said second time interval frequency is higher by a defined amount than the matched contraction frequency.

14. A device as claimed in claim 10 wherein said means for preventing a spontaneous contraction includes means for dividing said second time interval into successive first and second sub-intervals, said first sub-interval having a fixed duration and said second sub-interval having a duration which is set dependent on the duration of said first time interval by said means for automatically setting the duration of said second time interval and wherein said means for preventing a spontaneous contraction from starting a new first time interval starts a new second time interval only if a spontaneous tissue contraction is detected during said second sub-interval.

15. A device as claimed in claim 7 wherein said matched contraction frequency defines a matched contraction period, and said device further comprising means for setting the duration of said first time interval to correspond to said matched contraction period.

16. A device as claimed in claim 7 wherein said device is a heart pacemaker, wherein said means for detecting spontaneous tissue contractions is a means for detecting spontaneous heart muscle contractions, wherein said means for stimulating tissue contractions is a means for stimulating heart muscle contractions, and wherein said means for calculating a tissue contraction frequency matched to the physical activity of the patient is a means for calculating the heartbeat rate adapted to the physical activity of the patient.

17. A device as claimed in claim 7 wherein said device is a heart pacemaker, wherein said means for detecting spontaneous tissue contractions is a means for detecting spontaneous heart muscle contractions, wherein said means for stimulating tissue contractions is a means for stimulating heart muscle contractions, and wherein said means for calculating a tissue contraction frequency matched to the physical activity of the patient is a means for calculating the spontaneous heartbeat rate of the patient.

18. A method for administering electrical therapy to a patient, said method comprising the steps of:
  detecting spontaneous tissue contractions at a site in said patient;
  stimulating tissue contractions at said site at the end of a first time interval of selectable duration if a spontaneous tissue contraction is not detected during said first time interval;

starting said first time interval and starting a second time interval upon the occurrence of a spontaneous or stimulated contraction, said second time interval having a duration shorter than the duration of said first time interval;

preventing a spontaneous contraction from starting a new first time interval if said spontaneous contraction occurs during said second time interval;

starting a new second time interval upon the detection of a spontaneous contraction during said second time interval; and automatically setting the duration of said second time interval, dependent on the duration of said first time interval, when the duration of said first time interval is selected so that said second time interval is shorter than said first time interval by a defined amount.

19. A method for administering electrical therapy to a patient, said method comprising the steps of:

detecting spontaneous tissue contractions at a site in said patient;

stimulating tissue contractions at said site at the end of a first time interval of selectable duration if a spontaneous tissue contraction is not detected during said first time interval;

starting said first time interval and starting a second time interval upon the occurrence of a spontaneous or stimulated contraction, said second time interval having a duration shorter than the duration of said first time interval;

preventing a spontaneous contraction from starting a new first time interval if said spontaneous contraction occurs during said second time interval;

starting a new second time interval upon the detection of a spontaneous contraction during said second time interval;

calculating a tissue contraction frequency matched to the physical activity of the patient, the matched contraction frequency having a chronological curve associated therewith; and automatically setting the duration of said second time interval, dependent on the duration of said first time interval, when the duration of said first time interval is selected so that said second time interval has a chronological curve substantially following said chronological curve of said matched contraction frequency and is always shorter than said first time interval.

* * * * *